(12) United States Patent
Nam et al.

(10) Patent No.: US 8,101,369 B2
(45) Date of Patent: Jan. 24, 2012

(54) DIAGNOSE DEVICE FOR MEASURING THE RATIO OF PROTEINS WITH SIMILAR STRUCTURE

(75) Inventors: JungHyun Nam, Gyeonggi-do (KR); HyoJung Mo, Ansan-si (KR); WonJin Lee, Seoul (KR); JuHyun Han, Seongnam-si (KR); HeuiKeun Kang, Hwaseong-si (KR); JungHak Cha, Gunpo-si (KR); JinDong Chang, Seoul (KR); EunJeong Lim, Suwon-si (KR)

(73) Assignee: Humasis Co., Ltd. (KR)

( * ) Notice: Subject to any disclaimer, the term of this patent is extended or adjusted under 35 U.S.C. 154(b) by 410 days.

(21) Appl. No.: 11/920,582

(22) PCT Filed: May 23, 2006

(86) PCT No.: PCT/KR2006/001927
§ 371 (c)(1),
(2), (4) Date: Mar. 13, 2009

(87) PCT Pub. No.: WO2006/126821
PCT Pub. Date: Nov. 30, 2006

(65) Prior Publication Data
US 2009/0208983 A1    Aug. 20, 2009

(30) Foreign Application Priority Data

May 24, 2005    (KR) .......................... 10-2005-0043394

(51) Int. Cl.
*G01N 1/00* (2006.01)
*G01N 33/53* (2006.01)

(52) U.S. Cl. ............ 435/7.21; 435/2; 435/7.1; 436/501; 436/518; 436/522; 422/50; 530/300; 530/350; 424/130.1

(58) Field of Classification Search .......................... None
See application file for complete search history.

(56) References Cited

U.S. PATENT DOCUMENTS

| 5,786,220 A | 7/1998 | Pronovost et al. |
| 6,528,325 B1 | 3/2003 | Hubscher et al. |
| 2003/0124737 A1 | 7/2003 | O'Connor et al. |

FOREIGN PATENT DOCUMENTS

| WO | 02/13685 A1 | 2/2002 |
| WO | WO0213685 | 2/2002 |
| WO | 03/079011 A2 | 9/2003 |
| WO | 2005/031355 A1 | 4/2005 |

OTHER PUBLICATIONS

Determinants of Abnormal Gonadotropin Secretion in Clinically Defined Women With Polycystic Ovary Syndrom, Journal of Clinical Endocrinolgy and Metabolism, vol. 82,No. 7(1997).
European Search Report/Europen Search Opinion (PCT/KR2006/001927).
Clinical Chemistry, 38:3, 338-342 (1992).
Fertility and Sterility, vol. 65, No. 3, 517-522 (1996).
Journal of Clinical Endocrinology and Metabolism, 82:7, 2248-2256 (1997).
Clinical Chemistry, 46:1, 47-54 (2000).
Clinical Chemistry, 47:8, 1451-1457 (2001).
Euroanaylysis 13, Symposium S7-04 (2004).
Journal of Immunological Methods, 307, 1-12 (2005).

*Primary Examiner* — Lisa Cook
(74) *Attorney, Agent, or Firm* — Park & Associates IP Law, P.C.

(57) ABSTRACT

The present invention relates to a diagnostic device for measuring the ratio of similar structural proteins among the proteins secreted in a liquid test sample taken from diagnosis subject. In further detail, the test device according to the present invention comprises detection marker-antibody conjugate recognizing the same site on two or more similar structural proteins and a detection zone in which antibody specifically recognizes each of said proteins via formation of sandwich type complex, wherein said antibodies form a set, and the present Invention relates to a diagnostic device for early diagnosis of polycystic ovary syndrome, abnormal pregnancy, prostatic carcinoma etc. based on determination of the ratio of follicle stimulating hormone and luteinizing hormone in case of polycystic ovary syndrome, the ratio between hCG isomers in case of abnormal pregnancy, and the ratio of prostate-specific antigens (PSA) in case of prostatic carcinoma.

22 Claims, 11 Drawing Sheets

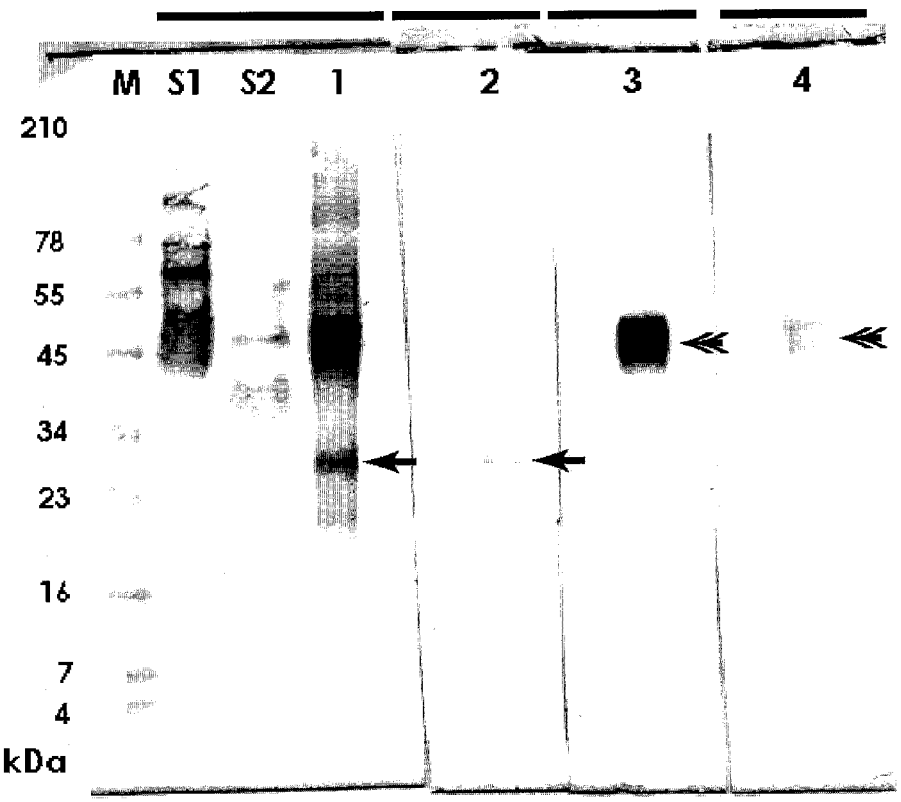

M, molecular weight marker ;
antibody 1(modified hCG-binding antibody 1)-S1, intact hCG standard; S2, beta hCG standard;
1, pregnant woman's urine sample;
antibody 2(modified hCG-binding antibody 2)-2, urine sample of pregnant woman;
antibody 3(intact hCG-binding antibody 1)-3, urine sample of pregnant woman;
antibody 4(intact hCG-binding antibody 2)-4, urine sample of pregnant woman;

symbol : ←, modified hCG(26kDa); ⇐, intact hCG

DIAGNOSE DEVICE FOR MEASURING THE RATIO OF PROTEINS WITH SIMILAR STRUCTURE

TECHNICAL FIELD

The present invention relates to a diagnostic device for determining the ratio of similar structural proteins in a test sample containing the similar structural proteins and to a diagnostic method for disease which can be diagnosed based on the ratio of similar structural proteins using the device.

BACKGROUND ART

As analytical methods for the secretion ratio of similar structural proteins in a test sample, enzyme immunoassay (EIA) and radioimmunoassay (RIA) etc. are currently used for quantitative determination of individual analyte, and the relative ratio is measured and used for a diagnosis of disease. However, because the methods as mentioned above carry out the analysis of analytes by using monoclonal antibody which recognizes specific epitope, the analytical result differs respectively according to analytical method, further shows a different numerical value in accordance with standard. As such, determination of the ratio based on analytical values showing difference even in a test sample of same patient naturally includes a large error, so it is hard to be used as objective clinical result.

It was known that polycystic ovary syndrome (PCOS) shows a high incidence of about 5% in teenagers and adults, respectively, and relatively common in fertile young women. The size of ovary in PCOS patients is 2-3 times larger than that of normal women, and about 10 small sacs are found therein. It has been reported that even in case of normal women, about 30% thereof shows polycystic ovary symptom on ultrasonography, yet in case of infertility patients, about 75% or more of the group shows PCOS symptom, causing repeated abortions. Further, it has been reported that an increase in frequency of solenoma and breast cancer due to continuous stimulation of estrogen, arteriosclerosis due to lipid change by raised female hormone level, and frequency of diabetes mellitus is high for accompanied hyperinsulinism. Also, PCOS is the most frequent cause for anovulation, and accompanied by fatal complications, indicating a clinical importance. PCOS is being diagnosed based on clinical symptoms, blood test or ultrasonography, and can be diagnosed by detecting abnormal menses such as oligomenorrhea or amenorrhea, clinical symptoms such as hypertrichosis, obesity, infertility and acne, and unbalance of female hormone level. PCOS is a disease which causes a variety of complications such as infertility when not suitably treated by screening in adolescent period.

Pertti et al. reported (Fertility & Sterility. 1996. 65(3):517-522) that as a method for differentiating polycystic ovary syndrome (PCOS) from normal women, comparative analysis on the level of luteinizing hormone (LH), follicle stimulating hormone (FSH), and androstenedio shows sensitivity of 98%, specificity of 93%. Tayler et al. reported that 75% or more of PCOS showed increased LH level, and 94% thereof showed a raise in the ratio of LH/FSH (J. Clinical Endocrinology & Metabolism. 1997. 82(7):2248-2256). As such, in a diagnosis of PCOS, the ratio between LH and FSH is used as significant result. However, such a method where the ratio of LH and FSH is determined after analyzing individual level of FSH and LH respectively by analytical instrument, is not suitable as a first screening method, thus at present, no analytical method is available by which PCOS-risk group can be early screened by one step test.

Korean Patent No. 0403871 discloses a device for diagnosing normal pregnancy and ectopic pregnancy, and manufacturing methods thereof, which device analyzes intact human chorionic gonadotrophin (hereafter, referred to as hCG) and modified hCG by using a combination of monoclonal antibodies. According to said disclosure, ectopic pregnancy is diagnosed based on measuring the ratio of intact hCG and modified hCG, where said similar structural proteins in test sample are assayed by use of different set of antibodies respectively. However, said Korean patent No. 0403871 has defects that an instant measurement of the ratio of the similar structural proteins is not possible because the ratio can only be determined after conducting individual analysis on the level of each protein by use of a different set of monoclonal antibodies.

Also, U.S. Pat. No. 5,786,220 discloses a manufacturing method for one-step diagnostic reagent which differentiates normal pregnancy and abnormal pregnancy, and describes that simultaneous determination of the levels of progesterone and hCG in female fluid enables diagnosis of normal pregnancy, abortion, ectopic pregnancy and cancer etc. That is, according to the disclosure, when the level of progesterone in blood is not more than 25 ng/ml and at the same time, that of hCG is in a range of 25-2,500 mIU/ml, diagnosed as spontaneous abortion and ectopic pregnancy, and when the level of progesterone in blood is 25 or more ng/ml and that of hCG is 2,500 or more mIU/ml, diagnosed as normal encyesis.

International Laid-open Publication No. 0070094 discloses a diagnostic method for trophoblast or non-trophoblast malignancy using antibody specifically reacting with early pregnancy associated molecular isoform (EPMI). According to the disclosure in said International Laid-open Publication No. 0070094, the levels of early pregnancy associated molecular isoform and intact form hCG in test sample are measured by reaction of early pregnancy associated molecular isoform and antibody, and the ratio between them is calculated, thereby to differentiate, normal pregnancy and abortion, trophoblastic disease and non-trophoblastic disease in early pregnancy.

Known methods as described above, that is, method of measuring doubling time of hCG level (during gestational ages of 5-9 weeks, blood level of hCG doubles every 1.4-2 days) and method of diagnosing ectopic pregnancy by measuring the level of free β-hCG in pregnant woman's fluid, are defective for necessity of repeated blood-collecting. Also a diagnostic principle of said methods differs from that of the present invention in that along with the measurement of hCG level, the level of progesterone should be also determined, and said methods include problems that though normal pregnancy and abnormal pregnancy can be differentiated, ectopic pregnancy which is very dangerous disease to pregnant women and spontaneous abortion are difficult to be effectively screened at an early stage.

On the other hand, prostate specific antigen (hereinafter, referred to as PSA) is a protein secreted from normal epithelial cell or cancer cell of prostate, and an enzyme which under normal situation acts to dissolve aggregated semen at the time of ejaculation. Though PSA is normally found only in prostate, when the normal structure of prostate is being destroyed due to tumor or infection, it is to be found even in blood stream. Further, in case of infection such as prostatitis or when prostate is enlarged for prostatomegaly yet not tumor, increased blood PSA level is observed. According to American Cancer Society, prostatic carcinoma has been reported to be the cancer most frequently diagnosed in men, and in 1999 about 179,300 cases of prostatic carcinoma were diagnosed and prostatic carcinoma shows a high death rate (37,000 persons) in men except lung cancer. Since PSA was lately found to have several molecular structures in blood serum, PSA test has been rapidly developed. The majority of PSA in blood serum binds with a variety of protease inhibitors, i.e. ACT (Alpha 1 antichymotrypsin) and AMT (alpha-2-macroglobulin). PSA-ACT conjugate is a major form in serum and called conjugate PSA. Another form of PSA is also found, enzymatically inactivated non-conjugate form with nothing bound. This is called free PSA. PSA test is performed via analysis of free PSA and total PSA, it was widely known that determining the ratio of free PSA can raise sensitivity and specificity of prostatic carcinoma. Measurement of free PSA is meaningful in that prostatic carcinoma and benign disease can be distinguished when prostatic carcinoma is not suspected on rectal examination yet the level of total PSA is 4.0-10.0 ng/ml. Also the lower the level of free PSA is, the higher the probability of prostatic carcinoma is, and thus measurement of free PSA can reduce unnecessary biopsy by 20-40%, and enables accurate diagnosis of tumor by specificity of 90% or more. Further Klaus (Clinical Chemistry, 2000. 46(1):47-54) et al. reported that tests on the ratio of PSA-ACT and free PSA are also used as marker to differentiate prostatic carcinoma and benign disease.

As described above, the known method performed two tests respectively and determined the ratio of similar structural proteins by comparing the analytical results, thus it has problem that standardization is impossible for a large variation of absolute value depending on the feature of diagnostic device.

DISCLOSURE OF THE INVENTION

Technical Problem

The present invention was devised to resolve the conventional problems as described above, and the object thereof resides in providing a diagnostic device for determining the ratio of similar structural proteins in a test sample containing the similar structural proteins, and to a diagnostic method for disease which can be diagnosed based on measuring the ratio of similar structural proteins by using the device.

Technical Solution

The present Invention relates to a diagnostic device and diagnostic method for measuring the ratio of similar structural proteins, and the present inventors noticed that the ratio of similar structural proteins among proteins secreted into human fluid can be analyzed, and the ratio can be used for diagnosis of disease, thereby to complete the present invention. That is, the present invention is effective in that the ratio of the levels of similar structural proteins present in a test sample can be evaluated on the basis of identical standard, and has advantage of quickness and simplicity of test.

The present invention relates to a diagnostic device for diseases that can be diagnosed based on the ratio of similar structural proteins, which is characterized in that it comprises a) a first probe-detection marker conjugate which is formed between a kind of probe having identical recognition site for two or more similar structural proteins and a detection marker, and b) two or more kinds of second probe, wherein each second probes recognize specifically each of the similar structural proteins, thereby forming a set of a) and b), each of said second probes being immobilized in spatially separate positions from each other(s), thereby to form a detect zone as a whole, said first probe-detection marker conjugate being provided either by being contained in a separate container or by being applied on a membrane pad such that it is free to migrate with aid of mobile phase, and the ratio of said similar structural proteins being able to be instantly read by simultaneous analysis for the reaction result of said similar structural proteins with said first and second probes, needless to conduct respective determination of the levels of each similar structural proteins in a test sample.

In the diagnostic device according to the present invention, it is preferred that said first and second probe are selected from a group consisting of monoclonal antibody, polyclonal antibody and lectin.

Said detection marker is preferred to be selected from a group consisting of radioisotope, enzyme, dye, magnetic bead, colloidal gold, selenium and latex bead.

In the diagnostic device according to the present invention, it is preferred that said test sample is preferred to be a liquid sample taken from test subject. As liquid sample, urine, saliva or blood can be exemplified.

Analytical method can be for example immunochromatography, enzyme linked immuno sorbent assay (ELISA), radio immunoassay, reverse passive hem agglutination (RPHA) and immunosensor etc.

It is preferred for the diagnostic device of the present invention that analytical method is immunochromatography method, it comprises a first pad and a second pad, in said first pad, said first probe-detection marker conjugate is provided as being applied in advance or just prior to the use such that said labeled conjugate can migrate by mobile phase, in said second pad, said second probes are immobilized in spatially separate positions from each other(s), thereby to form the detect zone. At this time, the device can further comprise a sample application pad and a sample absorbent pad.

The diagnostic device according to the present invention using immunochromatographic method is characterized in that
a) upon loading of said test sample onto said first pad, similar structural proteins including ones being the detect subject, competitively bind to said first probe-detection marker conjugate in accordance with relative amount (i.e. ratio) thereof in the test sample, thereafter
b) on reaching said second pad, said similar structural proteins being the detect subject, specifically bind to respective specific second probe, yielding a signal derived from the detection marker at the predetermined site of said second probe, thereby enabling the ratio of the similar structural proteins being the detect subject, to be read.

In addition, it is preferred for the diagnostic device of the present invention that analytical method is ELISA, and it comprises respective wells where the second probes are respectively immobilized, and a container containing the first probe-detection marker conjugate. The diagnostic device using ELISA method according to the present invention is characterized in that
a) on injecting a test sample into the container including said first probe-detection marker conjugate, the similar structural proteins being the detect subject, become competitively bound to said first probe-detection marker conjugate in accordance with the relative amount thereof in the sample, thereby forms a complex, and then,
b) on applying of said complex to each well where each specific second probes is immobilized respectively, each of said similar structural proteins being the detect subject, become respectively bound to specific second probe to be immobilized in each well, developing a detection marker-derived signal, thereby enabling the relative ratio of the similar structural proteins immobilized in each well to be read.

In the diagnostic device of the present invention, as disease that can be diagnosed based on the ratio of similar structural proteins, first, polycystic ovary syndrome can be enumerated, and in this case, similar structural proteins are luteinizing hormone and follicle stimulating hormone.

In the diagnostic device for polycystic ovary syndrome according to the present invention, the first probe is anti-luteinizing hormone monoclonal or polyclonal antibody or anti-follicle stimulating hormone monoclonal or polyclonal antibody which recognize the same site on luteinizing hormone and follicle stimulating hormone; the second probes could be anti-luteinizing hormone monoclonal antibody and anti-follicle stimulating hormone monoclonal antibody which respectively recognize specific site on each of luteinizing hormone and follicle stimulating hormone. In the diagnostic device of the present invention, as disease which can be diagnosed based on the ratio of similar structural proteins, secondly, abnormal pregnancy, ectopic pregnancy or abortion can be enumerated, and in this case, similar structural proteins are intact hCG and modified hCG.

Said modified hCG is preferred to be human placental hCG-related protein with a molecular weight of about 26 kDa.

In the diagnostic device for abnormal pregnancy, ectopic pregnancy or abortion according to the present invention, the first probe is anti-β-hCG monoclonal or polyclonal antibody which recognizes the same site on β subunit of intact hCG and modified hCG; the second probes could be anti-intact hCG monoclonal antibody and anti-modified hCG monoclonal antibody which respectively recognize specific site on each of intact hCG and modified hCG.

In the diagnostic device of the present invention, as disease that can be diagnosed by the ratio of similar structural proteins, thirdly, prostatic carcinoma or prostatomegaly can be enumerated, and in this case, similar structural proteins are free PSA and PSA-ACT.

In said diagnostic device for prostatic carcinoma or prostatomegaly according to the present invention, the first probe is anti-PSA monoclonal or polyclonal antibody which recognizes the same site on free PSA and PSA-ACT; the second probes could be anti free PSA monoclonal antibody and anti PSA-ACT monoclonal antibody which respectively recognize specific site on each of free PSA and PSA-ACT.

In addition, the present invention relates to a diagnostic method using the device as described above for disease that can be diagnosed based on the ratio of similar structural proteins. As example of such disease which can be diagnosed by the ratio of similar structural proteins, i) polycystic ovary syndrome (the similar structural proteins are luteinizing hormone and follicle stimulating hormone), ii) abnormal pregnancy, ectopic pregnancy or abortion (the similar structural proteins are intact hCG and modified hCG), and iii) prostatic carcinoma or prostatomegaly (the similar structural proteins are free PSA and PSA-ACT) can be mentioned.

Basic principle of the present invention is analytical method using a sandwich-type reaction among immunological assays, and as the nature of antibody used for such analytical method influences sensitivity and specificity of sample to be analyzed, suitable selection of antibody very important. For a sandwich assay, mostly two kinds of antibodies are used, and only when the binding sites of these two antibodies specific for antigen are present in spatially discrete position, sensitivity can be maintained. If the binding sites on the antibodies for antigen are too close or similar, sensitivity is lowered due to steric hindrance.

In further detail, the present invention is characterized in employing antibody having identical binding site for two or more similar structural proteins, and monoclonal antibody specifically binding to each of two or more similar proteins respectively; said antibody recognizing the identical site of the similar structural proteins is conjugated with a detection marker, and said monoclonal antibodies specifically binding to each of similar structural proteins are immobilized in suitable reaction site. That is, the present invention relates to diagnostic device for measuring the ratio of similar structural proteins in test sample, where upon application of a test sample containing similar structural proteins, said antibody recognizing identical site of said proteins becomes bound with the proteins according to the ratio of them, and monoclonal antibody specific to similar structural protein becomes then bound thereto following the ratio of similar structural proteins, thereby to form a sandwich type complex. Said labeled antibody which recognizes identical binding site of the similar structural proteins is monoclonal antibody or polyclonal antibody which recognizes every similar structural protein, and as specimen, fluid sample taken from test subject such as urine and blood is used.

In the present invention, as said detection marker, anyone selected from a group consisting of radioisotope, enzyme, dye, magnetic bead, colloidal gold, selenium and latex bead, can be used, and assays can be performed using immunochromatography, ELISA, radio immunoassay, reverse passive hemagglutination (RPHA) or immunosensor.

By using said diagnostic device of the present invention, polycystic ovary syndrome, abnormal pregnancy or prostatic carcinoma etc. can be early diagnosed by measuring the ratio of follicle stimulating hormone (FSH) and luteinizing hormone (LH) in case of polycystic ovary syndrome; the ratio of intact hCG and modified hCG in case of abnormal pregnancy; or the ratio of total prostate-specific protein and free prostate-specific protein in case of prostatic carcinoma.

One embodiment of the present invention is a method of using monoclonal antibody recognizing identical epitope on similar structural proteins and monoclonal antibody recognizing specific epitope on each of similar structural proteins, wherein said antibodies form a set. It is characterized in that said monoclonal antibody recognizing the same epitope is conjugated with signal-generating material such as colored particles or enzyme, and said monoclonal antibody recognizing specific epitope is immobilized on solid surface. As colored particles that can be used for the present invention, a variety of particles such as polystyrene particles, colloidal gold can be enumerated, and among them, colloidal gold is preferred, more preferably, colloidal gold in a range of 20-60 nm. Upon application of a test sample to said diagnostic device of the present invention, each of the similar structural proteins present in the test sample become bound to monoclonal antibody according to their respective ratio, and thus formed colored particles-monoclonal antibody-bound with each similar structural protein become then bound to the monoclonal antibody which recognizes different specific epitope on each of the similar structural proteins and is immobilized on solid surface, in accordance with the ratio within the sample. As such, the similar structural proteins bound to specific monoclonal antibody is detected according to their concentration, enabling the determination of the ratio of the similar structural proteins contained in the sample.

Such diagnostic device of the present invention is characterized in that at least three kinds of monoclonal antibodies are used, that is, one kind of monoclonal antibody recognizing same epitope on the similar structural proteins, and two kinds of different monoclonal antibodies recognizing specific epitope on each of the similar structural proteins.

Similar structural proteins present in the test sample of the present invention is characterized by containing at least one identical epitope, and different epitopes specific for each of the two or more proteins. As such similar structural proteins, intact hCG and modified hCG, luteinizing hormone and follicle stimulating hormone, PSA-ACT and free PSA can be enumerated.

The diagnostic device of the present invention is useful for determination of the ratio between similar antigens having similar structure, i.e. epitope which recognizes two or more antibodies. For example, it can be used for determination of the ratio of luteinizing hormone and follicle stimulating hormone in case of diagnosis of polycystic ovary syndrome, determination of the ratio of intact hCG and modified hCG in case of abnormal pregnancy diagnosis, and determination of the ratio of PSA-ACT and free PSA in diagnosis of prostatic carcinoma. Yet example of diagnosis using the analytical method of the present invention is not limited thereby. The diagnostic device of the present invention is based on understanding that similar hormones become bound to the detection marker-conjugated antibody which recognizes the same site of the similar hormones in accordance with the ratio in sample, thereby to form a detection marker-antibody-similar hormone complex, and this complex then become respectively bound to monoclonal antibody which has specificity toward each of the similar hormones and immobilized in detection zone, enabling instant detection of the level of similar hormones contained in the test sample, and as result of continuous research thereon, it was confirmed that said device is useful as a method by which polycystic ovary syndrome can be early screened by analyzing ratio of luteinizing hormone and follicle stimulating hormone, abnormal pregnancy such as ectopic pregnancy can be early screened by determining the ratio of intact hCG and modified hCG, and prostatic carcinoma and prostatomegaly can be differentiated in diagnosis of prostatic carcinoma based on the ratio of PSA-ACT and free PSA, leading to reduction of unnecessary biopsy causing serious adverse effects, thereby to complete the present invention.

In the present invention, the ratio of the similar structural proteins can be determined, since one kind of antibody recognizing identical binding site of similar structural proteins, is used, and each of the similar structural proteins present in the test sample spontaneously react therewith according to their respective ratio. That is, the amount of complex differs depending on the ratio between intact hCG and modified hCG, resulting in an instant determination of the ratio of similar structural proteins. In addition, in case of using the diagnostic device made as in the present invention for diagnosis of prostatic carcinoma, the ratio of PSA-ACT and free PSA can be analyzed by one-step manipulation, and based on this, benign disease can be screened from prostatic carcinoma, thereby to reduce unnecessary biopsy.

Method for determining the ratio of said similar hormones via use of the diagnostic device of the present invention is as follows. Example of the present diagnostic device is not restricted thereto, and this is explanation just for easy understanding of the present invention.

Construction and operation principle of the diagnostic device of the present invention is instantiated with FIGS. 1 to 10. FIG. 1 relates to testing method for the ratio of the similar structural proteins, and depicts steps of detection of the similar structural proteins, FIG. 2a shows immunochromatographic test device, one embodiment of the present invention.

This device contains one or more detection zone, and the detection zone comprises specific antibodies recognizing different binding site on similar structural proteins.

Among the diagnostic devices of the present invention, one embodiment using immunochromatographic method is as shown in FIG. 2a and a test strip which can perform a test is placed within a suitable plastic housing (1). The plastic housing contains a sample application aperture (2), a test result observation window (3), and test result lines (4), (5) and test end line (6). The test strip inserted into the plastic housing is prepared by fixing a nitrocellulose membrane on a suitable plastic plate and by immobilizing two kinds of monoclonal antibodies (11 and 12) having specificity to each of the similar proteins and test end line (13) showing extent of the test. Also an antibody-marker pad (9) containing antibody-marker conjugate is attached, which binds simultaneously with two or more similar structural proteins via binding to the same site on the similar structural proteins. When a test sample including similar structural proteins is applied to the sample application aperture (2) in FIG. 2a, each of the similar structural proteins becomes bound to detection marker-conjugated to antibody, respectively, to form a complex, and this complex become then bound to antibodies (11) and (12) immobilized on the nitrocellulose membrane according to the ratio of similar structural proteins in the sample, developing a color signal in accordance with the amount bound. If there is no protein in the sample of detect subject, no color signal appears at the test result line, and if similar protein presents in the sample, a color signal according to the ratio (2, 3, 4) will be developed at the test result line, enabling the ratio to be instantly read. Therefore in case of the diagnostic device for polycystic ovary syndrome in the present invention when the ratio of LH/FSH is 2.0 or more, it can be diagnosed as polycystic ovary syndrome, so it is designed that reaction sensitivity toward FSH was raised twice compared to that toward LH, so that equivalent color-generating rates might be produced at LH/FSH ratio of 2.0. Accordingly the cases (2) and (3) in FIG. 2c are read as LH/FSH ratio of 2.0 or more, being diagnosed as polycystic ovary syndrome, while case (4) in FIG. 2c is read as LH/FSH ratio of less than 2, being diagnosed as normal.

In addition, in case of diagnostic device for abnormal pregnancy as another embodiment of the present Invention, monoclonal antibody-marker conjugate was prepared by binding monoclonal antibody which recognizes the same epitope on both intact hCG and modified hCG with a marker such as colored particles and enzyme. This monoclonal antibody-marker conjugate becomes bound to both of two or more similar hormones, intact hCG and modified hCG, via recognizing the same epitope on them. In immunochromatographic method, a monoclonal antibody specific for intact hCG and a monoclonal antibody specific for modified hCG are respectively immobilized on the surface of membrane pad. Upon application of a test sample to thus prepared diagnostic device, according to the ratio of intact hCG and modified hCG in the sample, the similar hormones respectively bind to said monoclonal antibody-marker conjugate. Thus formed marker-monoclonal antibody-hCG complex migrates, becomes bound respectively to intact hCG-specific monoclonal antibody and modified hCG-specific monoclonal antibody immobilized on the membrane. As result, the ratio of similar structural proteins can be determined by one step based on the concentration of bound complex. In case of another embodiment, diagnostic device for prostatic carcinoma, for detection of free PSA and PSA-ACT, polyclonal antibody which can bind both of free PSA and PSA-ACT was conjugated with a marker. At test result line 1, monoclonal antibody having specificity to free PSA was immobilized and at test result line 2, monoclonal antibody specific for PSA-ACT was immobilized. Thus prepared test device can be used for determining the ratio of free PSA and PSA-ACT in a test sample.

As antibody used in the diagnostic device of the present invention, as shown in the following Table 1, for a device for polycystic ovary syndrome, as marker-conjugated antibody, one kind selected from anti α-luteinizing hormone antibody and anti α-follicle stimulating hormone antibody is used, which antibody can bind to the same site of luteinizing hormone and follicle stimulating hormone; as antibody immobilized on the detection zone, anti intact-luteinizing hormone monoclonal antibody and anti-intact-follicle stimulating hormone monoclonal antibody should be used respectively.

Further in the diagnostic device for measuring the ratio of intact hCG and modified hCG, antiβ-hCG antibody recognizing the same site on intact hCG and modified hCG is used for binding with a marker; as antibody immobilized on the detection zone, monoclonal antibodies respectively specific for each of anti-intact hCG and anti-modified-hCG are used.

In the diagnosis of prostatic carcinoma, as detection marker-conjugated antibody, anti-PSA monoclonal antibody is used, and as antibody immobilized on the detection zone, anti-free PSA antibody and anti-PSA-ACT antibody are used. By using a set of antibodies as described above, polycystic ovary syndrome, abnormal pregnancy (ectopic pregnancy), prostatic carcinoma can be early screened.

TABLE 1

Antibody used for diagnostic device for measuring the ratio of similar structural proteins

| Diagnosis | Detection marker-conjugated Antibody | Immobilized Antibody in detect zone 1 | Immobilized Antibody in detect zone 2 |
|---|---|---|---|
| Polycystic ovary syndrome | anti α-FSH antibody or anti α-LH antibody | anti intact-LH antibody | anti-intact-FSH antibody |
| Abnormal pregnancy | anti β-hCG antibody | anti-intact-hCG antibody | anti-modified-hCG antibody |
| Prostatic carcinoma | anti PSA monoclonal antibody | anti free PSA antibody | anti PSA-ACT antibody |

It will be apparent to those skilled in the art that the diagnostic device of the present invention can be applied for all immunoassays for measuring the ratio of similar structural proteins.

In further detail, the object of the present invention is to provide a diagnostic device in which a kind of antibody which binds with the similar structural proteins at an equal rate is used for binding with the similar structural proteins according to their individual ratio, and monoclonal antibody very specific to each of similar proteins is used for detecting the ratio of similar structural proteins specifically.

Also according to the present invention, the ratio of follicle stimulating hormone and luteinizing hormone having similar structure can be determined in polycystic ovary syndrome patient's fluid, the ratio of intact hCG and modified hCG can be instantly assayed in case of abnormal pregnancy. Moreover, in case of prostatic carcinoma, analysis of the ratio of PSA-ACT and free PSA enables diagnosis of prostatic cancer and differentiation between prostatic cancer and prostatomegaly at the same time.

BRIEF DESCRIPTION OF DRAWINGS

FIG. 2c shows an example of diagnosis by using the immunochromatographic device of FIG. 2a.

FIG. 3 is a result of western blot analysis on intact hCG and modified hCG in urine of pregnant woman, in case of diagnosis of abnormal pregnancy. M indicates molecular weight marker; antibodies 1 and 2, respectively represents modified hCG-binding antibody 1 and 2; antibodies 3 and 4, respectively represents intact hCG-binding antibody 1 and 2. Also SI means intact hCG standard, S2 means beta hCG standard, 1 to 4 respectively means urine specimen of pregnant woman.

MODE FOR CARRYING OUT THE INVENTION

Figure 1:
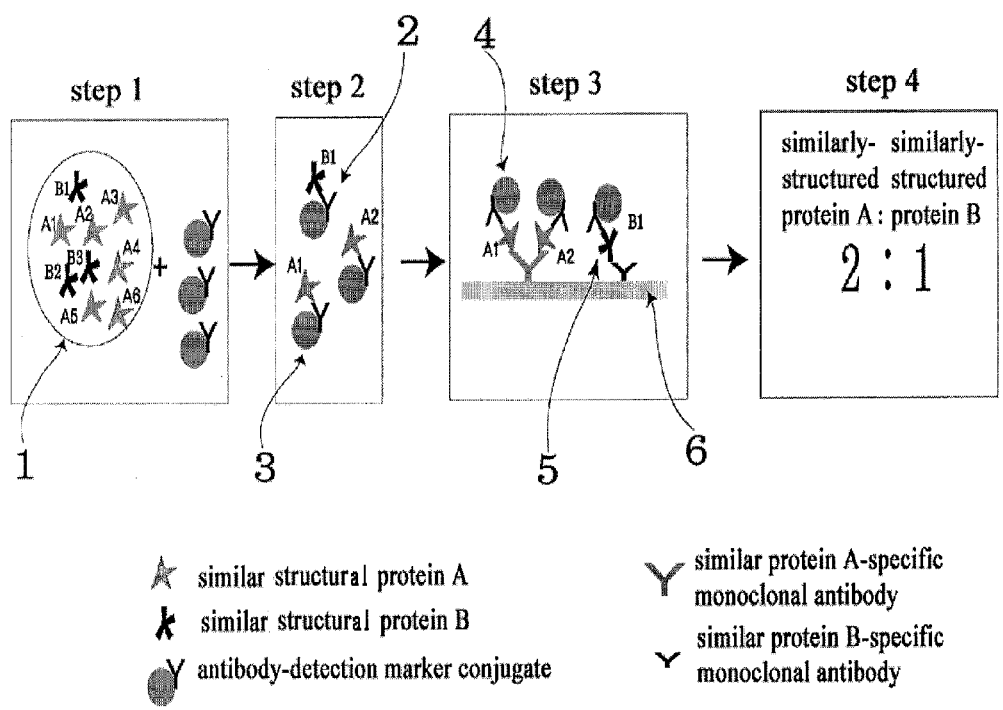
FIG. 1 relates to diagnostic method for the ratio of similar structural proteins according to the present invention, and depicts detection steps for the similar structural proteins. No. 1 means a test sample containing two or more similar structural proteins; 2 and 3 respectively represents the formation of complex which is formed by binding of the similar structural proteins with detection marker-conjugated antibody according to their respective ratio; 4 and 5 respectively represents formation of a sandwich type complex which is formed by binding of immobilized antibody specific for each protein with said complex (2 and 3); and 6 represents a support part of detection zone.
Figure 2A:
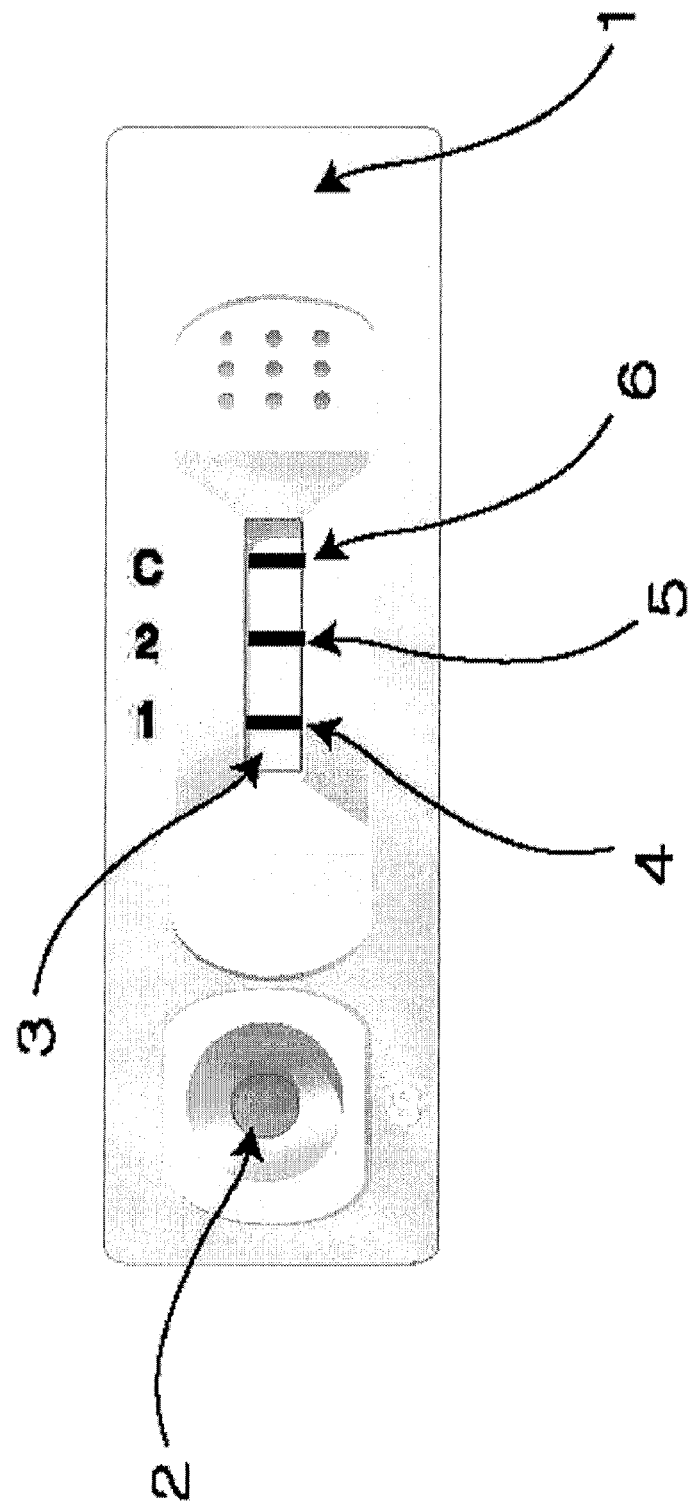
FIG. 2a shows an immunochromatographic test device prepared according to the diagnostic method of the present invention. No. 1 represents a plastic housing, 2 represents a sample application aperture, 3 represents test result observation window, and 4, 5 and 6 represent respectively test result line 1, test result line 2 and test end line (C).
Figure 2B:
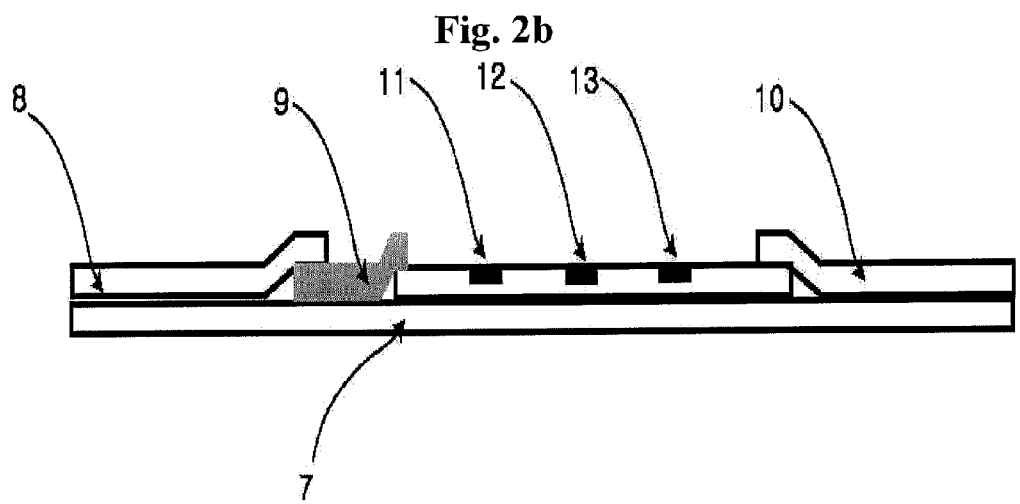
FIG. 2b shows a test strip inserted in said plastic housing of FIG. 2a. No. 7 is an adhesive support plate, 8 is a sample dripping pad, 9 is a pad containing antibody-detection marker conjugate, 10 is a sample absorbent pad, 11 and 12 are respectively test result line 1, test result line 2, and 13 is a test end line.
Figure 2C:
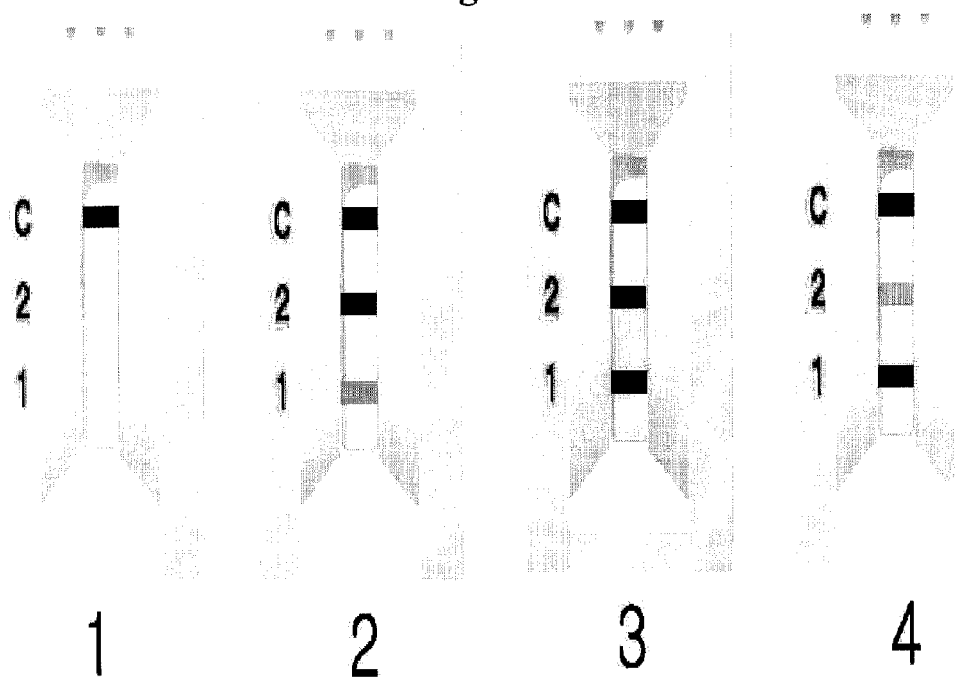

The present invention is to be explained in more detail with examples. These examples just specifically describe the present invention, and it will be apparent to those skilled in the art that the scope of the present invention is not limited thereby.

EXAMPLE 1

Preparation of Monoclonal Antibody

Monoclonal antibody used for the present invention can be directly prepared in the present invention or purchased among commercially available ones. Immunization and cell fusion was performed according to known cell fusion method (Galfre, G et al. 1981, Methods Enzymol. 73:3-46). First, Balb/C mouse (8 weeks) was provided and FSH, LH, intact hCG, modified hCG, free PSA and PSA-ACT (respectively 20 μg/100 μl) were completely emulsified with Freund's complete adjuvant 100 μl and were given by first intraperitoneal injection, and by the same method, after 3 weeks, second intraperitoneal injection was given by emulsifying with Freund's incomplete adjuvant 100 μl. After 1 week, blood sample was taken from the mouse, and whether antibody is formed or not was identified by immunochromatographic method, then said proteins (20 μg) were respectively given by intravenous injection. After 3 days, spleen cell of the mouse was taken and fused with pre-incubated Sp2/0 cell by using PEG. Thus fused cell was added to HAT culture solution and cell which secretes suitable antibody was screened while incubating in 96 well. Large scale-culture solution was centrifuged, precipitate was removed, supernatant was collected and allowed to pass through protein A-sepharose FF, washed in phosphate buffer, and eluted with 0.1M glycine buffer. Eluate was subjected to dialysis against phosphate buffer, adjusted to an appropriate concentration and used for preparation of diagnostic device.

EXAMPLE 2

Characteristic Assay of Monoclonal Antibody

A. Characteristic assay by Indirected ELISA

In order to explain reaction features of respective antibodies used in the present invention, indirected ELISA was used. In microtiter 96 well plate, each of the similar hormones was diluted with phosphate buffered saline (1 μg/well) and added (100 μl) to coating buffer (0.1M carbonate buffer, pH 9.5) and reacted at 37° C. for 2 hrs. When the reaction was completed, the reaction solution was treated with immuno washer and washed with washing solution (phosphate buffered saline, 0.05% Tween 20, 0.1% sodium azide) three times, 300 μl of blocking solution (0.2% casein/PBS) was added and subjected to a reaction for 3 hrs at room temperature. After the reaction was finished, the resultant things were washed 3 times with washing solution. 100 μl of monoclonal antibody-HRP (horse radish peroxide) conjugate of the present invention, was added to each well to 1 μg/well and 2 μg/well concentration, respectively. After a reaction at 4° C. for two hours, added HRP-conjugate solution was discarded and washed 3 times with washing solution. Color reagent of HRP-substrate kit (Bio-Rad, USA) was added (100 μg/well) and reacted for 10 min. After finishing of reaction, 100 μl/well of stop solution (3% oxalic acid) was added, and $A_{45}0$ was measured with automatic ELISA reader (BIO-Rad, USA).

Table 2 discloses features of monoclonal antibody prepared in the present invention, yet the features of the antibody described in the Table 2 does not restrict the scope of the present invention. In addition, in preparing diagnostic device using the monoclonal antibody of the present invention, application position of each antibody can be changed, that is, immobilized antibodies at detection zone 1 and 2 except the detection marker-conjugated antibody can be exchanged with each other, having no influence to performance of the diagnostic device.

TABLE 2

Comparison of reaction characteristics of antibody set by indirected ELISA

| Diagnosis | Classification | Marker-conjugated Ab | Immobilized Ab in detection zone 1 | Immobilized Ab in detection zone 2 |
|---|---|---|---|---|
| Polycystic ovary syndrome | Antibody | Anti-αFSH or -α LH antibody | Anti-intact-LH antibody | Anti-intact-FSH antibody |
| | Response (%) | α-FSH (100%) α-LH (100%) β-FSH (<1%) β-LH (<1%) TSH (<1%) | FSH (100%) LH (<1%) TSH (<1%) | FSH (<1%) LH (100%) TSH (<1%) |
| Abnormal pregnancy | Antibody | anti-βhCG antibody | anti intact-hCG antibody | anti modified-hCG antibody |
| | Response (%) | I-hCG (100%), modified hCG (100%), LH (<1%), TSH (<1%), FSH (<1%) | i-hCG (100%), modified hCG (<10%) LH (<1%) TSH (<0.1%) FSH (<1%) | i-hCG (<1%), modified hCG (100%) LH (<1%) TSH (<0.1%) FSH (<1%) |
| Prostatic carcinoma | Antibody | anti-PSA antibody | anti-freePSA antibody | anti PSA-ACT antibody |
| | Response (%) | free PSA (100%) PSA-ACT (100%) | free PSA (100%) PSA-ACT (<1%) | free PSA (<1%) PSA-ACT(100%) |

B. Characteristic Assay by Western Blot Analysis

Whether the antibodies applied for the abnormal pregnancy-testing device can detect intact hCG and modified hCG in pregnant woman's fluid, was confirmed through the ratio test of intact hCG and modified hCG according to the present invention, and for this, intact hCG standard (S1), beta hCG standard (S2) and urine samples of normal pregnancy women (1,2,3,4) were subjected to SDS-gel electrophoresis, transferred to nitrocellulose membrane, and then allowed to bind respectively to monoclonal antibodies (antibodies 1,2,3,4) which were used for measuring the ratio of intact hCG and modified hCG. Then second antibody (goat anti-mouse IgG- HRP) was allowed to bind, color reagent was used to detect the band of protein-monoclonal antibody complex.

As shown in FIG. 3, in case of antibody 1 and antibody 2 i.e. the antibody set reacting with modified hCG respectively, only modified hCG was detected; while in case of antibody 3 and antibody 4, i.e., intact hCG-binding antibody, intact hCG reacted with both of the two antibodies, thereby revealing that each of the monoclonal antibodies specifically binds modified hCG or intact hCG. Furthermore, it was found that when as modified hCG, hCG-related protein of about 26 kDa taken from pregnant woman's urine was used, abnormal pregnancy could be more clearly diagnosed. This means that in case of using about 26 kDa of hCG-related protein for diagnosis of abnormal pregnancy, its reactivity is larger than that of other molecular weight protein, producing more obvious result by a single test, thereby indicating the use of specific monoclonal antibody thereto is of utility industrially.

EXAMPLE 3

Characteristic Assay by ELISA Diagnostic Device

A. Verification of the Ratio of Similar Structural Proteins by Using ELISA Device In ELISA device for determining the ratio of similar proteins, monoclonal antibodies which specifically recognize each of the proteins with similar hormone to be assayed were immobilized in two reaction wells (sample well 1, sample well 2).

Antibody which recognizes identical site on the two similar structure hormones, that is, anti-α-FSH/LH monoclonal antibody for diagnosis of polycystic ovary syndrome, anti-β-hCG monoclonal antibody for diagnosis of abnormal pregnancy, and anti-PSA monoclonal antibody for diagnosis of prostatic carcinoma, were respectively bound with HRP (horse radish peroxide) to prepare monoclonal antibody-detection marker conjugate.

In the sample wells 1 and 2, anti-β-FSH monoclonal antibody and anti-β-LH monoclonal antibody for diagnosis of polycystic ovary syndrome; anti intact-hCG monoclonal antibody and anti modified-hCG monoclonal antibody for diagnosis of abnormal pregnancy; and anti-free PSA monoclonal antibody and anti-PSA-ACT monoclonal antibody for diagnosis of prostatic carcinoma, were respectively used. Said monoclonal antibodies were diluted to 10 µg/ml, 20 ug/ml, and added (100 µl) respectively to coating buffer (0.1M carbonate buffer, pH 9.5) and reacted at 37° C. for 2 hrs, washed 3 times with washing solution (phosphate buffered saline, 0.05% Tween 20, 0.1% sodium azide), 300 µl of blocking solution (0.2% casein/PBS) was added and reacted at room temperature for 3 hrs. After the reaction, the reaction solution was washed 3 times with washing solution and, dried to prepare ELISA kit for measuring the ratio of similar structural proteins.

Figure 4:
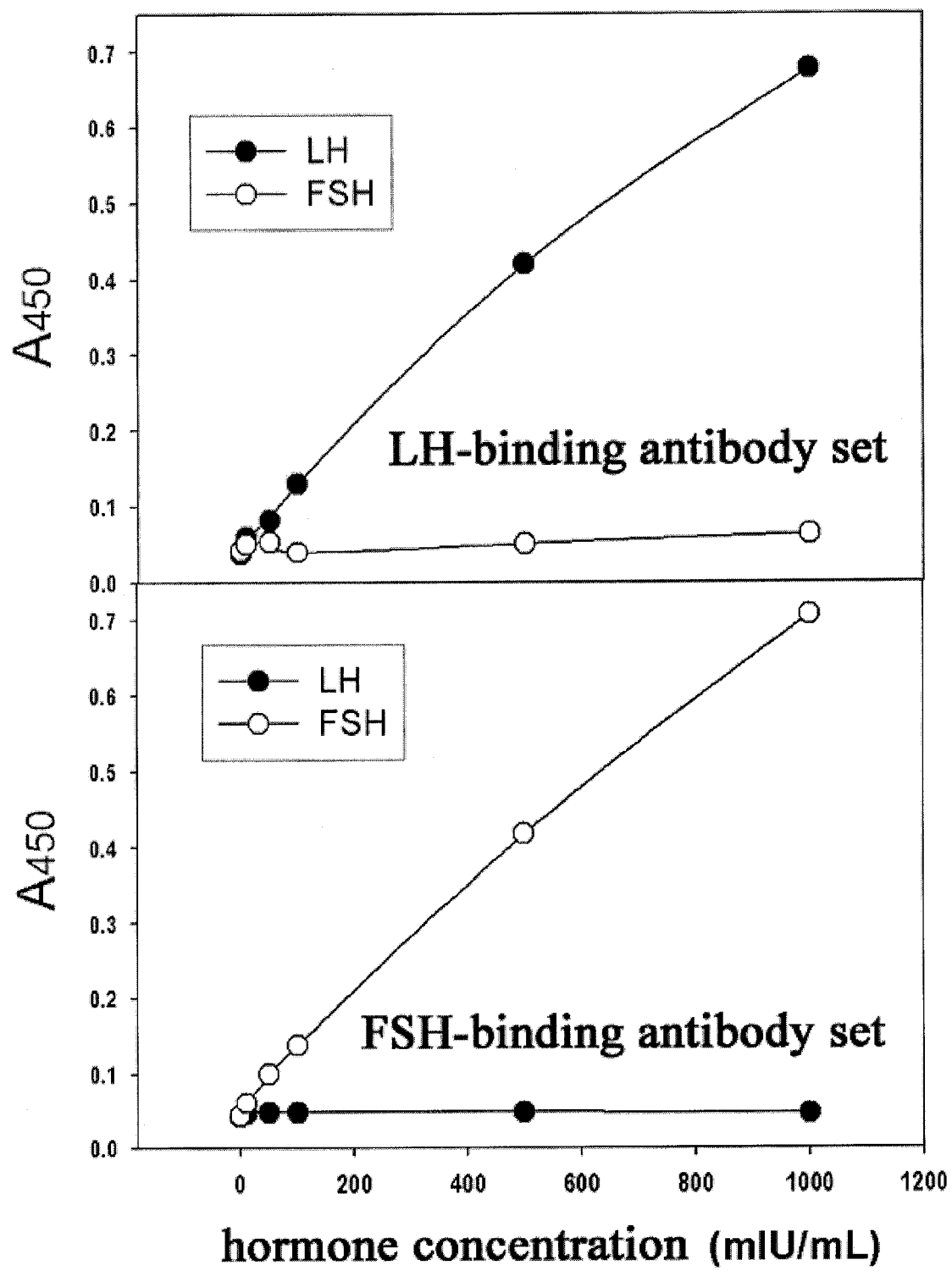
FIG. 4 shows a standard curve for test result of indirected ELISA in diagnosis of polycystic ovary syndrome, where labeled antibody and specific monoclonal antibody immobilized on detection zone were used for measuring the ratio of luteinizing hormone and follicle stimulating hormone.
Figure 5:
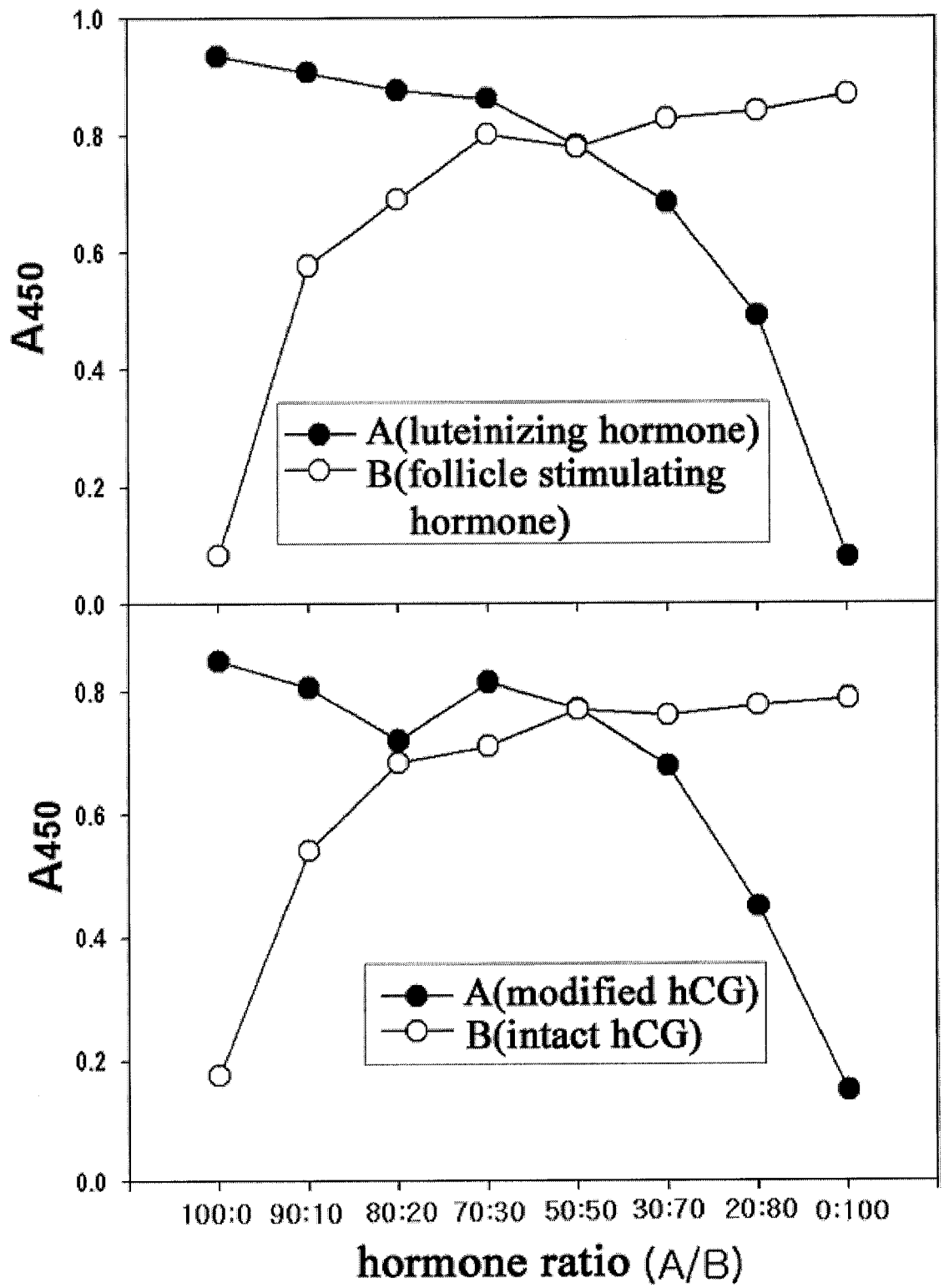
FIG. 5 shows test result of indirected ELISA carried out for test samples which were prepared to contain various ratios of luteinizing hormone and follicle stimulating hormone, intact hCG and modified hCG.

Among thus prepared indirected ELISA diagnostic devices, in case of that for polycystic ovary syndrome, as result of performing the test on luteinizing hormone and follicle stimulating hormone of various concentrations by respectively using a set of anti-α-FSH/LH antibody and anti intact-LH antibody, a set of anti-α-FSH/LH antibody and anti-intact-FSH antibody, anti LH antibody set detected only LH, anti FSH antibody set detected only FSH, as shown in FIG. 4. As can be seen in FIG. 5, even in specimen prepared to contain various ratios between similar proteins, i.e. ratio of LH/FSH and ratio of modified hCG/intact hCG, the antibody set applied for testing devices for polycystic ovary syndrome and abnormal pregnancy, without failure, detected accurate ratio of the corresponding similar structural proteins.

B. Verification of the Ratio of Modified hCG in Diagnosis of Abnormal Pregnancy

To determine distribution of the concentration of modified hCG for screening abnormal pregnancy in pregnant women and to confirm its clinical efficiency, sandwich ELISA method using intact hCG-binding antibody set and modified hCG-binding antibody set was carried out. In specimen of normal pregnancy and ectopic pregnancy cases, 40 cases of normal pregnancy were selected among the patients whose intrauterine gestational sac were confirmed on ultrasonography in infertility clinic or prenatal clinic, and whose cyematocardia was later confirmed by a follow-up, and the cases of missed abortion, incomplete or complete abortion during a follow-up were excluded from the test group. 25 cases of ectopic pregnancy were selected among the patients who were transferred from other hospital under suspected ectopic pregnancy or were confirmed not to have gestational sac by a follow-up from infertility clinic or prenatal clinic, and later diagnosed as ectopic pregnancy on biopsy after laparoscopic surgery.

In case of normal pregnancy group, urine specimen was taken at the time of first confirming intrauterine gestational sac on ultrasonography, in case of ectopic pregnancy group, urine and blood sample (50 cc and 3 cc, respectively) were collected from patients at the time of confirming ectopic pregnancy by eye on abdominoscopy, and stored under freezing at −20° C. before use, and then measurement of the level of intact hCG and modified hCG in the urine and blood sample was conducted.

Figure 6:
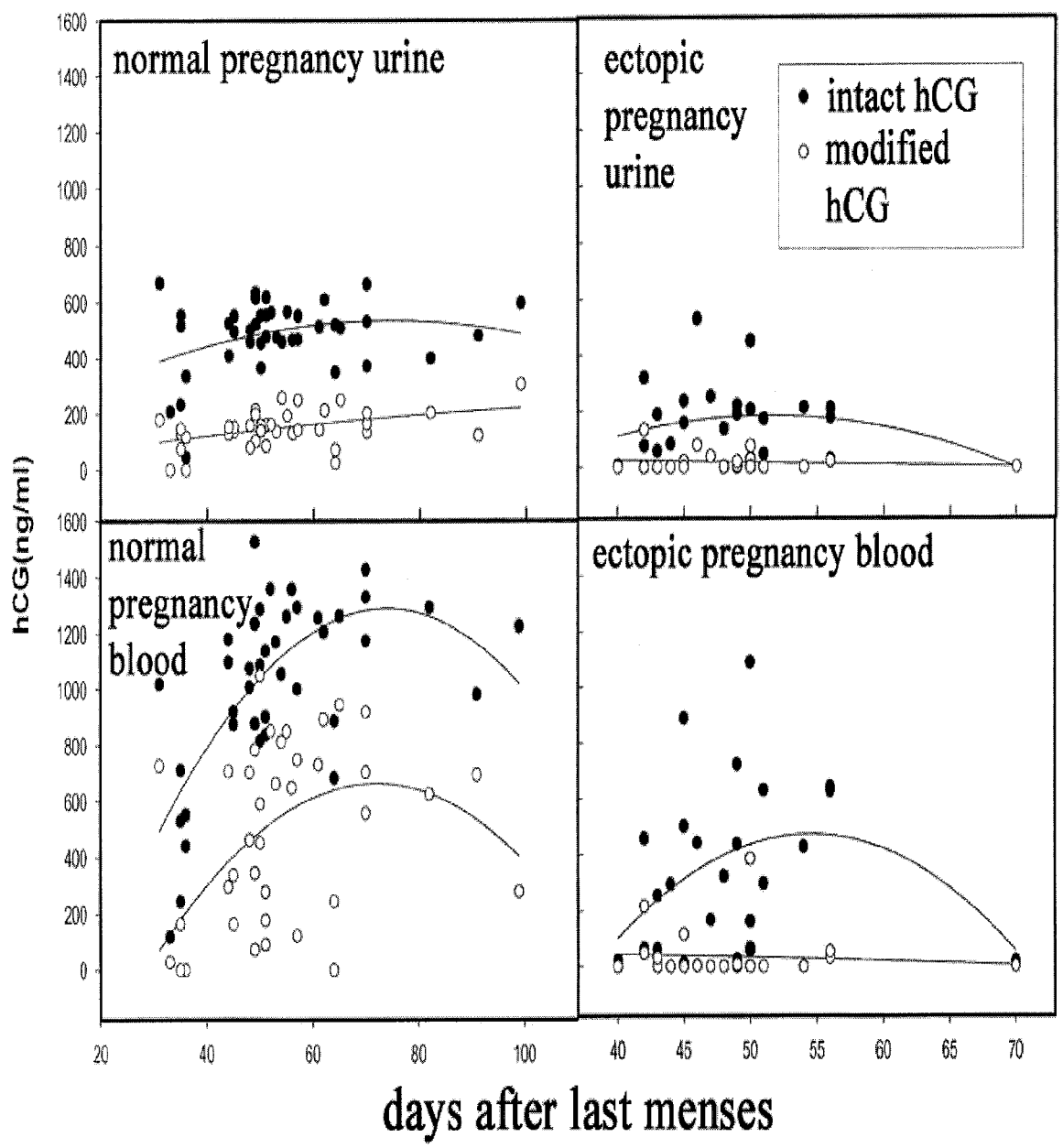
FIG. 6 represents distribution result of intact hCG and modified hCG in normal and abnormal pregnancy specimen, which was obtained from indirected ELISA using intact hCG-binding antibody set and modified hCG-binding antibody set in diagnosing abnormal pregnancy.

As shown in FIG. 6, in the urine sample for normal pregnancy, the level of intact hCG and modified hCG were 486±19.9 ng/ml, 149±10.2 ng/ml, respectively, and that of the blood sample were 1,018+50.3 ng/ml, 468±51.6 ng/ml, respectively. In addition, in the urine sample for ectopic pregnancy, the level of intact hCG and modified hCG were 160+ 27.4 ng/ml, 14.1±6.6 ng/ml, respectively, and that of blood sample were 350±17.5 ng/ml, 35.9+17.5 ng/ml, respectively. According to said result, it was demonstrated that level of modified hCG in ectopic pregnancy was significantly decreased in comparison with that of normal pregnancy.

Figure 7:
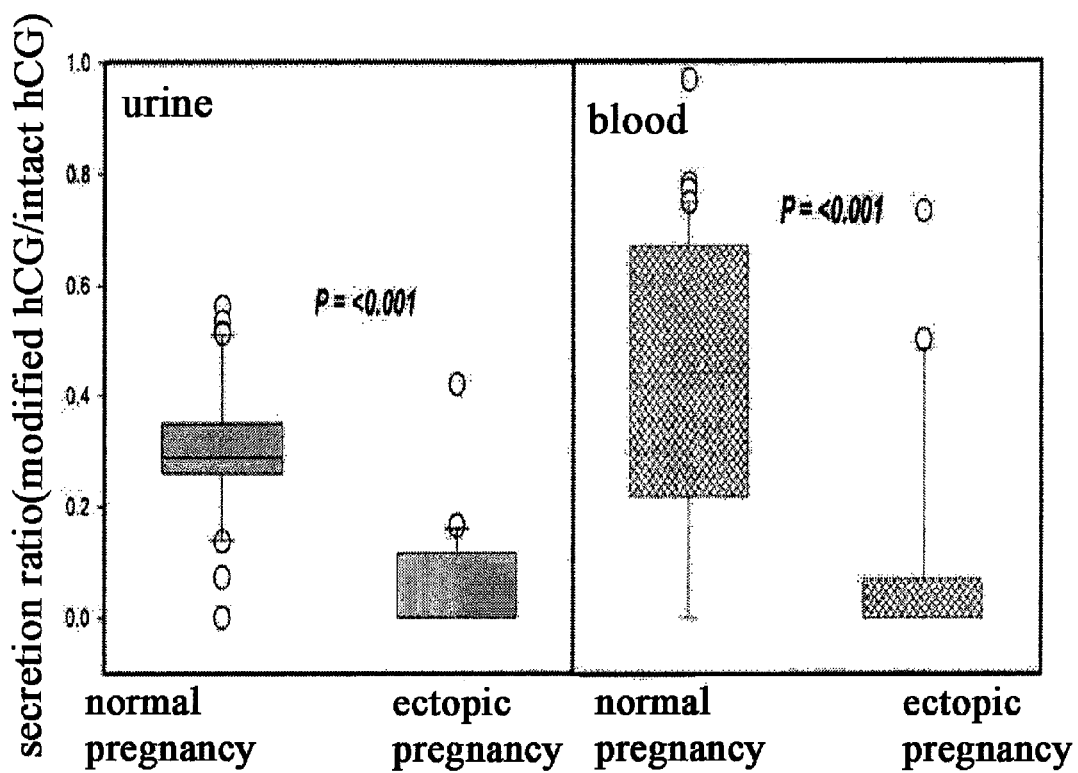
FIG. 7 shows distribution of the ratio of modified hCG and intact hCG in urine and blood sample of normal pregnancy and ectopic pregnancy case.

FIG. 7 illustrates a secretion ratio of modified hCG and intact hCG in urine and blood samples of normal pregnancy and ectopic pregnancy cases, wherein the respective ratio in each sample showed a significant difference, revealing that normal encyesis group and ectopic pregnancy group can be effectively differentiated. The following Table 3 shows a comprehensive result on the concentration distribution and secretion ratio of modified hCG and intact hCG in clinical test group.

TABLE 3

Comparison of concentration distribution of modified hCG and intact hCG in diagnosis of abnormal pregnancy (ectopic Pregnancy)

| Classification | Encyesis (case no. = 40) | Ectopic pregnancy (case no. = 25) | p value |
|---|---|---|---|
| Age(years) | 29.5 ± 0.43 | 29.8 ± 0.75 | NS(0.68) |
| Days after last menses | 50.2 ± 1.23 | 48.6 ± 1.65 | NS(0.49) |
| Blood intact hCG(ng/ml) | 1,018 ± 50.3 | 350 ± 59.4 | <0.001 |
| Blood modified hCG (ng/ml) | 468 ± 51.6 | 35.9 ± 17.5 | <0.001 |
| Blood modified hCG/intact hCG (%) | 42.2 ± 4.2 | 9.5 ± 4.0 | <0.001 |

TABLE 3-continued

Comparison of concentration distribution of modified hCG and intact hCG in diagnosis of abnormal pregnancy (ectopic Pregnancy)

| Classification | Encyesis (case no. = 40) | Ectopic pregnancy (case no. = 25) | p value |
|---|---|---|---|
| Urine intact hCG(ng/ml) | 486 ± 19.9 | 160 ± 27.4 | <0.001 |
| Urine modified hCG(ng/ml) | 149 ± 10.2 | 14.1 ± 6.6 | <0.001 |
| Urine modified hCG/intact hCG (%) | 29.7 ± 1.9 | 4.6 ± 1.9 | <0.001 |

Abbreviation: NS, no significance

Figure 8:
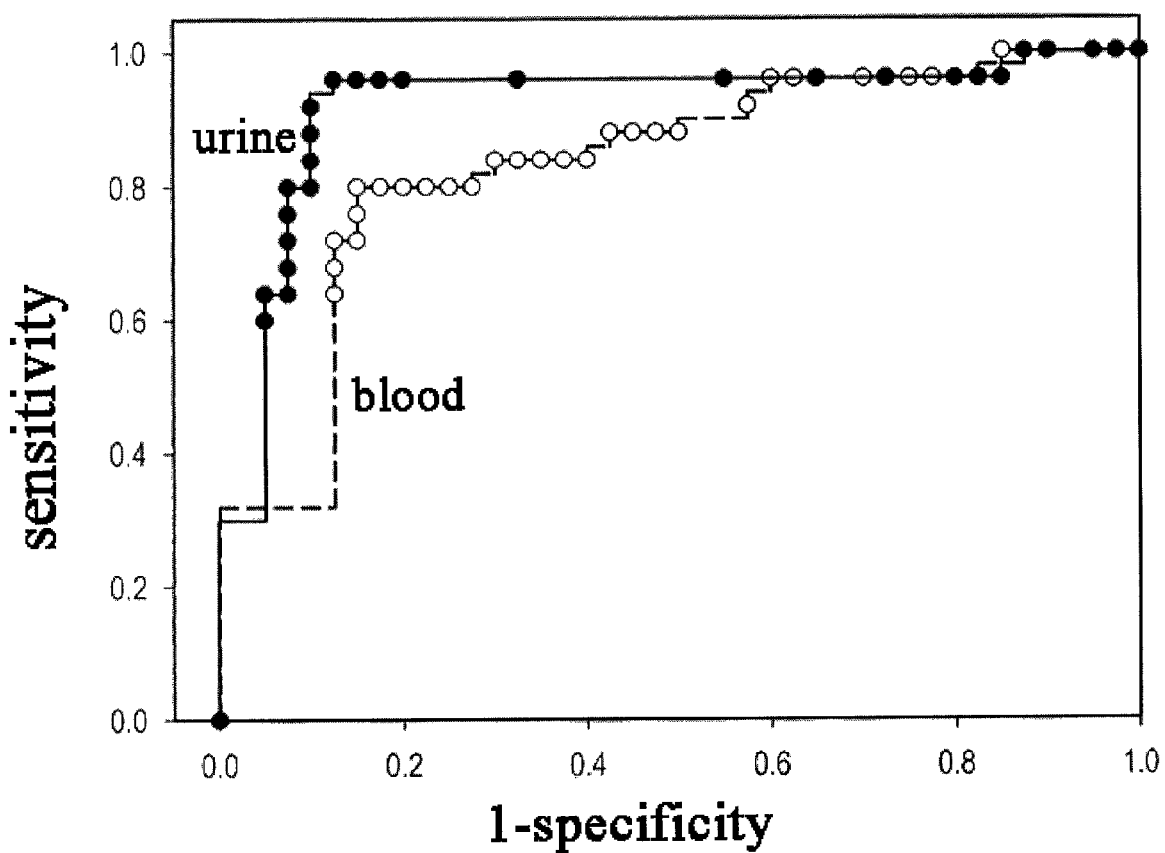
FIG. 8 represents ROC curve indicating sensitivity and specificity of ratio test on modified hCG and intact hCG in normal pregnancy and ectopic pregnancy cases.

FIG. 8 is ROC curve representing sensitivity and specificity in diagnosing abnormal pregnancy (ectopic pregnancy) which was derived from various secretion ratios of modified hCG and intact hCG. According to said result, when criterion having a power of discrimination in urine and blood samples is considered to be 16.2% and 9%, the sensitivity and specificity in urine were 92% and 90% respectively, and in case of blood samples, 80% and 85% respectively. It could be confirmed when the ratio of modified hCG and intact hCG according to the present invention is employed as criterion, a very high diagnosis rate can be obtained.

EXAMPLE 5

Preparation of the Diagnostic Device of the Present Invention Using Immunochromatography A. Preparation of Colloidal Gold (Colored Particles)

Colored particles used in the present invention was prepared with colloidal gold in a range of 20-60 nm. For the preparation, secondary distilled water (220 ml) was added to a 500 ml of round flask. The flask was placed on a hot plate (Corning, USA) and a reflux apparatus was installed to prevent evaporation of steam. On the hot plate, the reaction flask was heated to 100° C. while suspending. When the temperature of distilled water reached 100° C. or more, 1.0 ml of 2% gold chloride (Sigma, USA), was added thereto, completely mixed, then vigorously mixed with addition of 2.0 ml of 1% sodium citrate (Sigma, USA). By further heating for 30 min, the formation of colloidal gold was induced. Thus prepared colloidal gold was filtered through 0.45 μm filter paper to remove impurities and coagulated substance, and used for preparing the diagnostic device of the present invention.

B. Preparation of Immunochromatographic Diagnostic Device

To prepare monoclonal antibody conjugated with colored particles, as colored particles, 50 ml of colloidal gold was added to respective beaker. While stirring, anti-β-hCG monoclonal antibody or anti-α-FSH monoclonal antibody or anti-PSA monoclonal antibody was added to 1~15 μg per colored particles 1 ml, and subjected to a further reaction for 20 to 30 min. After the reaction, 1% to 10% bovine serum albumin or sodium casein-containing blocking solution was added to each beaker to a final concentration of 0.1~1% and reacted for 20~30 min. Said reaction solution was placed in 50 ml of centrifuge tube (Corning, USA) and centrifuged (Backman, USA) at 10,000 rpm for 10~20 min. After the centrifugation, supernatant was discarded, pellet was collected and suspended in stabilizing solution [0.5-2% bovine serum albumin, 1-5% sucrose, 50~10 OmM Tris buffer (pH 7.5-9.0)]. Said suspension was adjusted to an appropriate concentration, immersed in a colored particles pad and dried. To prepare an antibody-immobilized membrane, at the site of test result line 1, an appropriate amount of anti-intact hCG monoclonal antibody or anti-β-FSH monoclonal antibody or anti-free PSA monoclonal antibody, was applied and immobilized. At the site of test result line 2, an appropriate amount of, anti modified hCG monoclonal antibody or anti-β-LH monoclonal antibody or anti-PSA-ACT monoclonal antibody was respectively applied and immobilized. At the test end line, anti-mouse immunoglobulin G polyclonal antibody was immobilized. A sample application pad (glass fiber, Millipore Corp., USA) or cellulose paper (Whatman, USA) was used, and as a sample absorbent pad, cellulose paper (Whatman, USA) was used. Thus prepared monoclonal antibody-colored particles pad, antibody-immobilized membrane, sample application pad and sample absorbent pad are arranged on a polyester supporting plate such that said antibody-colored particles conjugate pad is partially superimposed with antibody immobilized pad, said sample application pad is partially superimposed in length of 1-10 mm with the labeled antibody-containing pad, and said sample absorbent pad is partially superimposed in length of 1-5 mm with immobilized antibody-pad, thereby to construct the test strip for measuring the ratio of similar structural proteins. The test strip prepared as described above was placed into a suitable plastic housing and constructed, thereby to complete diagnostic device for polycystic ovary syndrome, abnormal pregnancy and prostatic carcinoma according to the present invention, respectively. In immunochromatographic diagnostic device for measuring the ratio of similar structural proteins in the present invention, in case of the one for polycystic ovary syndrome, the device was prepared such that the LH/FSH ratio of 1.5-2.3 or more is diagnosed as positive (polycystic ovary syndrome), less than 1.5-2.3, is diagnosed as negative (normal), and in case of the test device for abnormal pregnancy, it was prepared such that the ratio of modified hCG/intact hCG in a range of less than 0.1-0.5 is diagnosed as positive (abnormal pregnancy), the ratio between 0.1-0.5 or more is diagnosed as negative (normal pregnancy). Additionally, in case of the test device for prostatic carcinoma and prostatomegaly, it was prepared such that the ratio of less than 0.1-0.25 is diagnosed as positive (prostatic carcinoma), the ratio of 0.1-0.25 or more is diagnosed as negative (prostatomegaly).

Figure 9:
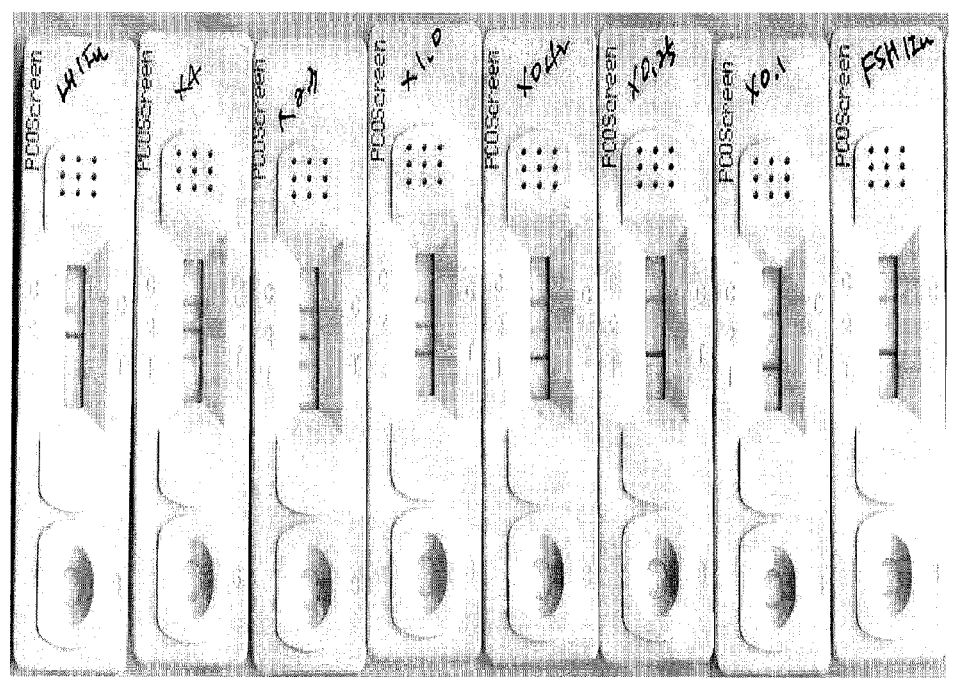
FIGS. 9 and 10 represent respectively test result and graph thereof, which test was performed on test samples containing various ratios of luteinizing hormone and follicle stimulating hormone by using PCOS test device according to the present invention.

FIG. 9 represents diagnosis result of the immunochromatographic test device for polycystic ovary syndrome. In relation with the ratio of LH/FSH, at a ratio of 2.3 or more, color intensity developed at LH-detecting line is stronger than that of FSH line, thereby to be diagnosed as positive, while at a ratio of 1.0 or less, the color intensity of LH line is weaker than that of FSH line, thereby to be diagnosed as negative. Said result can be proposed as actual example showing that immunochromatographic test device, one embodiment of the present invention, performs accurate determination of the ratio of similar structural proteins, thus can be utilized for diagnosis of disease.

Figure 10:
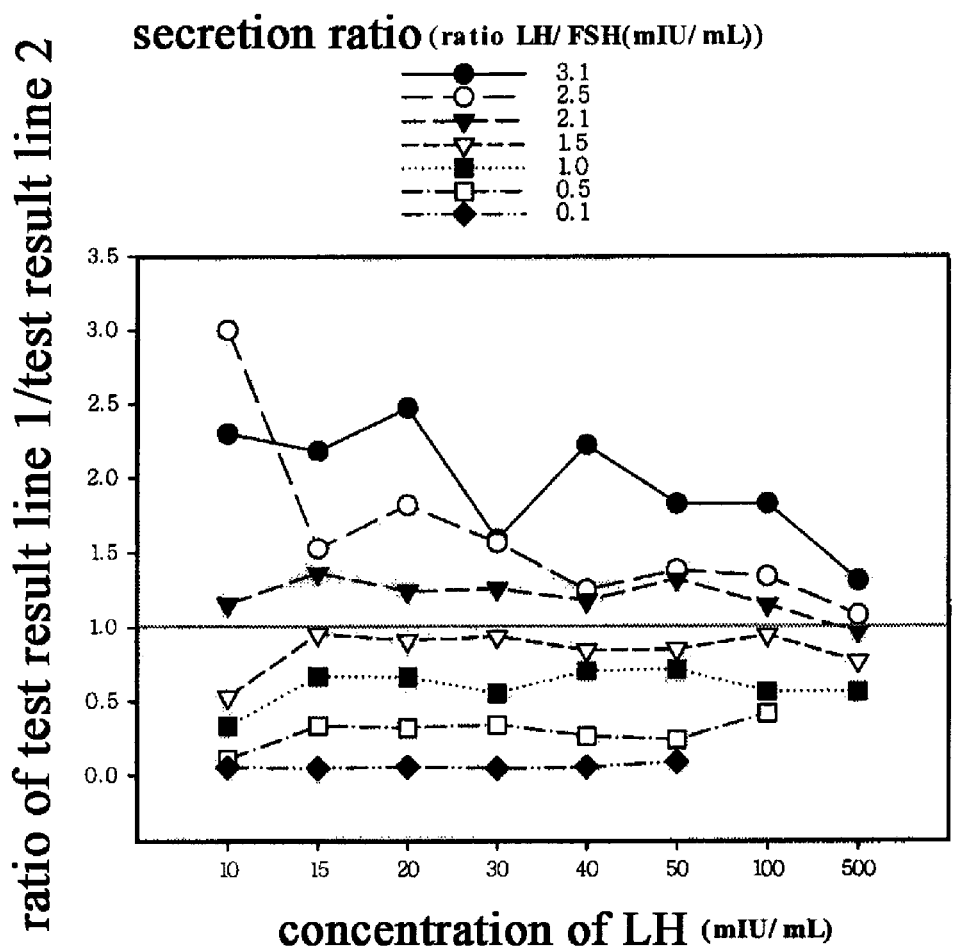

The ratio of luteinizing hormone and follicle stimulating hormone was determined for test samples having more various concentration ratios by using the immunochromatographic test device of the present invention, and the result is as shown in Table 4 and FIG. 10. Test solutions were respectively prepared to have the ratio of luteinizing hormone and follicle stimulating hormone in a range of 0.1-3.1, and were tested by the immunochromatographic device. As result, at concentrations where the ratio is 2.1 or more, it could be diagnosed as positive, and at concentrations where the ratio is 1.5 or less, diagnosed as negative. That is, when the ratio between luteinizing hormone and follicle stimulating hormone is 2.1 or more, an identical result with the secretion ratio of hormones in polycystic ovary syndrome, could be obtained, indicating that secretion ratio in normal women is 1.5 or less.

TABLE 4

Luteinizing hormone and follicle stimulating hormone Concentration ratio of LH/FSH (mIU/mL/mIU/mL)

| 2.5/0.8 | 2.5/1.0 | 2.5/1.2 | 2.5/1.7 | 2.5/2.5 | 2.5/5 | 2.5/25 |
|---|---|---|---|---|---|---|
| 5.0/1.7 | 5.0/2.0 | 5.0/2.4 | 5.0/3.3 | 5.0/5.0 | 5.0/10 | 5.0/50 |
| 10/3.3 | 10/4.0 | 10/4.8 | 10/6.7 | 10/10 | 10/20 | 10/100 |
| 15/5.0 | 15/6.0 | 15/7.1 | 15/10 | 15/15 | 15/30 | 15/150 |
| 20/6.7 | 20/8.0 | 20/9.5 | 20/13.3 | 20/20 | 20/40 | 20/200 |
| 30/10 | 30/12 | 30/14.3 | 30/20 | 30/30 | 30/60 | 30/300 |
| 40/13.3 | 40/16 | 40/19 | 40/26.7 | 40/40 | 40/80 | 40/400 |
| 50/16.7 | 50/20 | 50/23.8 | 50/33.3 | 50/50 | 50/100 | 50/500 |
| 100/33.3 | 100/40 | 100/47.6 | 100/66.7 | 100/100 | 100/200 | — |
| 500/166.7 | 500/200 | 500/238.1 | 500/333.3 | 500/500 | — | — |
| ratio of 3.1 | ratio of 2.5 | ratio of 2.1 | ratio of 1.5 | ratio of 1.0 | ratio of 0.5 | ratio of 0.1 |
| disease positive | disease positive | disease positive | disease negative | disease negative | disease negative | disease negative |

INDUSTRIAL APPLICABILITY

The diagnostic device of the present invention is effective in that the ratio of the similar structural proteins in a test sample can be instantly determined. This test device can be utilized for early diagnosis and large scale screening of abnormal pregnancy, polycystic ovary syndrome and prostatic carcinoma etc. by determining the ratio of follicle stimulating hormone and luteinizing hormone in case of polycystic ovary syndrome, the ratio of intact hCG and modified hCG in case of abnormal pregnancy and the ratio of total PSA and free PSA in case of prostatic carcinoma.

The invention claimed is:

1. A diagnostic device for diseases that can be diagnosed based on the ratio of similar structural proteins, which is characterized in that it comprises
   a) a first probe-detection marker conjugate which is formed between a kind of probe having identical recognition site for two or more similar structural proteins and a detection marker, and
   b) two or more kinds of second probe, wherein each second probes recognize specifically each of the similar structural proteins,
   thereby forming a set of a) and b),
   each of said second probes being immobilized in spatially separate positions from each other(s), thereby to form a detect zone as a whole,
   said first probe-detection marker conjugate being provided either by being contained in a separate container or by being applied on a membrane pad such that it is free to migrate with aid of mobile phase, and
   the ratio of said similar structural proteins being able to be instantly read by simultaneous analysis for the reaction result of said similar structural proteins with said first and second probes, needless to conduct respective determination of the levels of each similar structural proteins in a test sample.

2. The diagnostic device according to claim 1, wherein said first and second probe are selected from a group consisting of monoclonal antibody, polyclonal antibody and lectin.

3. The diagnostic device according to claim 1, wherein said detection marker is selected from a group consisting of radioisotope, enzyme, dye, magnetic bead, colloidal gold, selenium and latex bead.

4. The diagnostic device according to claim 1, wherein said test sample is a liquid sample taken from test subject.

5. The diagnostic device according to claim 4, wherein said liquid sample is urine, saliva or blood.

6. The diagnostic device according to claim 1, wherein said analytical method is immunochromatography, enzyme linked immuno sorbent assay (ELISA), radio immunoassay, reverse passive hemagglutination (RPHA) or immunosensor.

7. The diagnostic device according to claim 6, wherein said analytical method is immunochromatography method and,
   the device comprises a first pad and a second pad,
   wherein in said first pad, said first probe-detection marker conjugate is provided as being applied in advance or just prior to the use such that said probe-detection marker conjugate can migrate by mobile phase, and in said second pad, each of said second probes are immobilized in spatially separate positions from each other(s), thereby to form the detect zone.

8. The diagnostic device according to claim 7, wherein it further comprises a sample application pad and a sample absorbent pad.

9. The diagnostic device according to claim 7, which is characterized in that
   a) upon loading of said test sample onto said first pad, similar structural proteins including ones being the detect subject, competitively bind to said first probe-detection marker conjugate in accordance with relative amount (i.e. ratio) thereof in the test sample, thereafter
   b) on reaching said second pad, said similar structural proteins being the detect subject, specifically bind to respective specific second probe, yielding a signal derived from the detection marker at the predetermined site of said second probe, thereby enabling the ratio of the similar structural proteins being the detect subject, to be read.

10. The diagnostic device according to claim 6, wherein said analytical method is ELISA, and it comprises respective wells where said second probes are respectively separately immobilized, and a container containing said first probe-detection detection marker conjugate.

11. The diagnostic device according to claim 10, characterized in that
   a) on injecting a test sample into the container including said first probe-detection marker conjugate, the similar structural proteins being the detect subject, become competitively bound to said first probe-detection marker conjugate in accordance with the relative amount thereof in the sample, thereby forms a complex, and then,
   b) on applying of said complex to each well where said each specific second probes is immobilized respectively, each of said similar structural proteins being the detect subject, become respectively bound to specific second probe to be immobilized in each well, developing a detection marker-derived signal, thereby enabling the relative ratio of the similar structural proteins immobilized in each well to be read.

12. The diagnostic device according to claim 1, wherein said disease that can be diagnosed based on the ratio of similar structural proteins is polycystic ovary syndrome, and
   said similar structural proteins are luteinizing hormone and follicle stimulating hormone.

13. The diagnostic device according to claim 12, wherein said first probe is anti-luteinizing hormone monoclonal or polyclonal antibody or anti-follicle stimulating hormone monoclonal or polyclonal antibody which recognizes the same site on luteinizing hormone and follicle stimulating hormone, and said second probes are anti-luteinizing hormone monoclonal antibody and anti-follicle stimulating hormone monoclonal antibody which respectively recognize specific site on each of luteinizing hormone and follicle stimulating hormone.

14. The diagnostic device according to claim 1, wherein said disease which can be diagnosed based on the ratio of similar structural proteins is abnormal pregnancy, ectopic pregnancy or abortion, and said similar structural proteins are intact hCG and modified hCG.

15. The diagnostic device according to claim 14, wherein said modified hCG is human placental hCG-related protein with a molecular weight of about 26 kDa.

16. The diagnostic device according to claim 14, wherein said first probe is anti-β-hCG monoclonal or polyclonal antibody which recognizes the same site on β subunit of intact hCG and modified hCG, and said second probes are anti-intact hCG monoclonal antibody and anti-modified hCG monoclonal antibody which respectively recognize specific site on each of intact hCG and modified hCG.

17. The diagnostic device according to claim 1, wherein said disease that can be diagnosed by the ratio of similar structural proteins is prostatic carcinoma or prostatomegaly, and said similar structural proteins are free PSA and PSA-ACT.

18. The diagnostic device according to claim 17, wherein said first probe is anti-PSA monoclonal or polyclonal antibody which recognizes the same site on free PSA and PSA-ACT, and said second probes are anti free PSA monoclonal antibody and anti PSA-ACT monoclonal antibody which respectively recognize specific site on each of free PSA and PSA-ACT.

19. A diagnostic method for disease that can be diagnosed based on the ratio of similar structural proteins, wherein the device as described in claim 1 is employed.

20. The diagnostic method according to claim 19, wherein said disease which can be diagnosed by the ratio of similar structural proteins is polycystic ovary syndrome, and said similar structural proteins are luteinizing hormone and follicle stimulating hormone.

21. The diagnostic method according to claim 19, wherein said disease which can be diagnosed by the ratio of similar structural proteins is abnormal pregnancy, ectopic pregnancy or abortion, and said similar structural proteins are intact hCG and modified hCG.

22. The diagnostic method according to claim 19, wherein said disease which can be diagnosed by the ratio of similar structural proteins is prostatic carcinoma or prostatomegaly, and said similar structural proteins are free PSA and PSA-ACT

* * * * *